United States Patent [19]

Chen et al.

[11] Patent Number: 5,714,635
[45] Date of Patent: Feb. 3, 1998

[54] METHOD FOR PREPARING CYLCOHEXYLAMINE

[75] Inventors: Yin-Zu Chen, Chung-Li; Zhang-Feng Yang, Taipei; I-Hui Chen, Kaohsiung, all of Taiwan

[73] Assignee: San Fu Chemical Co., Ltd., Taipei, Taiwan

[21] Appl. No.: 758,142

[22] Filed: Nov. 25, 1996

[30] Foreign Application Priority Data

Jun. 6, 1996 [TW] Taiwan .................................. 85106761

[51] Int. Cl.$^6$ .................................................. C07C 209/72
[52] U.S. Cl. ............................................................ 564/450
[58] Field of Search ....................................... 564/450, 462

[56] References Cited

U.S. PATENT DOCUMENTS

| | | | |
|---|---|---|---|
| 3,891,707 | 6/1975 | Waddan | 260/583 K |
| 4,384,142 | 5/1983 | Merten et al. . | |
| 4,914,239 | 4/1990 | Kiyuma et al. . | |
| 4,935,505 | 6/1990 | Townsend et al. | 536/24 |
| 4,943,549 | 7/1990 | Immel et al. . | |
| 5,023,226 | 6/1991 | Immel et al. . | |
| 5,599,997 | 2/1997 | Hearn et al. | 564/450 |
| 5,637,593 | 6/1997 | Porter et al. | 514/274 |

FOREIGN PATENT DOCUMENTS

| | | |
|---|---|---|
| 4207314 | 9/1993 | Germany . |
| 64-70446 | 3/1989 | Japan . |

*Primary Examiner*—Brian M. Burn
*Attorney, Agent, or Firm*—Dennison, Meserole, Pollack & Scheiner

[57] ABSTRACT

The present invention is related to a method for preparation of cyclohexylamine by hydrogenating aniline at a temperature of 150° to 250° C. under a hydrogen pressure of 1 to 20 atm in the presence of a catalyst selected from a chromium- or thorium- modified cobalt boride, wherein the amount of said modified cobalt boride is at least 0.6 wt % based on the weight of aniline.

Compared with the prior art which used a conventional hydrogenation catalyst such as ruthenium, palladium, Raney cobalt or Raney nickel, the method adopted by the present invention has the advantages in that it can be performed under a relatively lower hydrogen pressure without necessity of adding any coupling inhibitors and a much higher aniline conversion and a higher or comparable selectivity to cyclohexylamine can be obtained, thus resulting in greatly increased yield of cyclohexylamine.

7 Claims, No Drawings

METHOD FOR PREPARING CYLCOHEXYLAMINE

FIELD OF THE INVENTION

The present invention is related to a novel process for the preparation of cyclohexylamine by hydrogenating aniline in the presence of a catalyst selected from a chromium- or thorium-modified cobalt boride.

BACKGROUND OF THE INVENTION

Cyclohexylamine is used in synthesis of sodium cyclamate and calcium cyclamate, which are used as artificial sweetener. It can also be used in the industrial applications such as boiler water-treating agent, rubber accelerator or rust inhibitor. Further, Cyclohexylamine is an important intermediate in industrial chemical synthesis.

So far, there have been lots of published literature reporting the processes for preparation of cyclohexylamine. Most of them involved in hydrogenation of aniline in the presence of a catalyst selected from noble metals such as ruthenium and palladium, wherein a pressure up to tens or hundreds of atmospheres was usually required. Such high pressure was disadvantageous from the viewpoint of safety and requirement of expensive equipments. Moreover, in the process of hydrogenation of aniline, the intermediates such as enamines and imines may be formed and these intermediates may further react with aniline or cyclohexylamine to form coupling by-products such as N-phenylcyclohexylamine or dicyclohexylamine. Accordingly, large amount of anhydrous ammonia was usually used to inhibit these coupling reaction during hydrogenation of aniline. However, addition of anhydrous ammonia will not only make the design of the reaction-system complicated but also cause problems in the treatment and discharge of waste gas. Therefore, it is important to reduce the pressure without reducing the yield and the selectivity in transforming aniline to cyclohexylamine.

U.S. Pat. No. 4,384,142 issued to Monsanto Company disclosed a process for preparation of cyclohexylamine by hydrogenation of aniline at a temperature ranging from 160° to 180° C. under a hydrogen pressure ranging from 20 to 50 atm in the presence of a ruthenium catalyst, wherein anhydrous ammonia was used as a coupling inhibitor.

German Patent No. 4,207,314 issued to BASF Company disclosed a process for preparation of cyclohexyamine by hydrogenation of aniline at 160° C. in the presence of a catalyst composed of a mixture of ruthenium, palladium and magnesium and a carrier selected from barium carbonate, wherein anhydrous ammonia was used as a coupling inhibitor in a ratio of ammonia to hydrogen of 2:3. It was reported that, after 24 hours of reaction, the ratio of cyclohexylamine to dicyclohexylamine in the resulting product was 88.6:11.

German Patent No. 3,824,822 issued to Bayer Company disclosed a process for preparation of cyclohexylamine by hydrogenation of aniline at a temperature of 200° C., under a hydrogen pressure as high as 280 atm, in the presence of a manganese- and cerium-modified ruthenium catalyst, wherein no coupling inhibitors were used. As a result, dicyclohexylamine, a coupling by-product, was up to 58.3% of the total amount of the product.

German Patent No. 3,801,755 disclosed a high-pressure process for preparation of cyclohexylamine, wherein aniline was hydrogenated at a temperature of 109° C. under a hydrogen pressure of 280 atm in the presence of a ruthenium-palladium catalyst which has been modified by manganese and chromium. The ratio of cyclohexylamine to dicyclohexylamine in the resulting product was reported to be 91.1:8.8.

Japanese Patent No. 64,70,446 issued to New Japan Chemical Co. disclosed a process for preparation of cyclohexylamine by hydrogenation of aniline at a temperature of 190° C. under a hydrogen pressure of 7 atm in the presence of 50% nickel/diatomaceous earth as a catalyst, wherein anhydrous ammonia was used as a coupling inhibitor in a ratio of ammonia to hydrogen of 1:5. The resulting product contained 75% cyclohexylamine.

The above processes of the prior art has to either use large amount of anhydrous ammonia as coupling inhibitor or be operated at an extremely high pressure, e.g. 280 atm. The use of anhydrous ammonia as a coupling inhibitor may make the reaction system complicated and causes troubles in the treatment and discharge of waste gas. Further, reaction under a high-pressure needs to be carried out in a high pressure-resistant equipment, which is usually expensive, and it is disadvantageous from the standpoint of safety. In addition, the selectivity to cyclohexylamine in most of these prior processes is unsatisfactory, which results in large amount of by-products.

OBJECTIVES OF THE PRESENT INVENTION

An objective of the present invention is to provide a novel process for preparing cyclohexylamine from aniline in the presence of a catalyst selected from a chromium- or thorium- modified cobalt boride, which can significantly enhance the conversion percentage of aniline when compared with the prior processes wherein a conventional hydrogenation catalyst such as ruthenium, palladium, Raney cobalt or Raney nickel was used.

Another objective of the present invention is to provide a novel process for preparing cyclohexylamine from aniline in the presence of a catalyst selected from a chromium- or thorium-modified cobalt boride, wherein a high selectivity to cyclohexylamine can be obtained without addition of any coupling inhibitors, thus hydrogenation process and waste gas treatment can be simplified.

A further objective of the present invention is to provide a novel process for preparing a cyclohexylamine from an aniline in the presence of a catalyst selected from a chromium- or thorium- modified cobalt boride, which can be carried out under a pressure as low as 20 atm or less, thus the expensive equipment for a high pressure process is not required and the problems in safety can be minimized.

DETAILED DESCRIPTIONS OF THE PRESENT INVENTION

In order to solve the problems encountered in the prior art as mentioned above, the present inventors made extensive research in these processes. It has been found that when a transition metal-modified metal boride was used as a catalyst, the reaction could be performed under a relatively lower pressure and in absence of any coupling inhibitors. Also, a high conversion percentage of aniline and a high selectivity to cyclohexylamine could be obtained.

It has also been found that, under a hydrogen pressure lower than 20 atm and in absence of a coupling inhibitor, use of a nickel boride modified by chromium, thorium or molybdenum as a catalyst resulted in an enhanced conversion percentage of aniline by several times when compared with some conventional catalysts such as a ruthenium or palladium catalyst. However, said conversion percentage was only slightly higher than or comparable to that obtained by a Raney-nickel catalyst.

To our surprise, a cobalt boride modified by chromium or thorium resulted in a much higher conversion percentage of aniline, which was two or more times as high as that obtained by a conventional Raney-nickel catalyst, as well as a high selectivity (for example, 90 mol %) to cyclohexylamine, which was comparable to that of a Raney-nickel catalyst. The cobalt boride modified by molybdenum showed less activity than a Raney-nickel catalyst in enhancing the conversion of aniline and hence was not preferred.

Owing to the above observations, the present inventors propose a novel method for preparation of a cyclohexylamine, which comprises hydrogenating an aniline at a temperature of 150° to 250° C. under a hydrogen pressure of 1 to 20 atm in the presence of a catalyst selected from a chromium- or thorium-modified cobalt boride, wherein said modified cobalt boride is used in an amount of at least 0.6 wt % based on the weight of aniline.

The modified cobalt boride for used in the present invention is produced by modification of a cobalt boride catalyst with an organic or inorganic salt of chromium or thorium, wherein the amount of chromium in a chromium-modified cobalt boride is generally 0.5–15 wt %, preferably 2–10 wt %, more preferably 2–8 wt %, based on the weight of cobalt boride; and the amount of thorium in a thorium-modified cobalt boride is generally 0.1–20 wt %, preferably 2–15 wt %, more preferably 2–10 wt %, based on the weight of cobalt boride.

In the present method, the modified cobalt boride is generally used in an amount of at least 0.6 wt %, preferably 0.6–20 wt %, more preferably 2.0–15 wt %, based on the weight of aniline. If the amount of the modified cobalt boride is lower than 0.6 wt %, the conversion percentage of aniline is usually unsatisfactory. There is no specific upper limit for the amount of the modified cobalt boride. The modified cobalt boride can be used repeatedly.

In the present method, the reaction temperature is generally in a range of 150°–250° C., preferably 150°–230° C., and more preferably 160°–230° C. The temperature lower than 150° C. cannot result in a satisfactory conversion percentage of aniline. On the other hand, the temperature higher than 250° C. may significantly decrease the selectivity to cyclohexylamine, consequently resulting in increase of the coupling by-products.

In the present method, the hydrogen pressure is generally in a range of 1 to 20 atm, and preferably 3 to 20 atm. The hydrogen pressure lower than 1 atm cannot result in a satisfactory conversion percentage of aniline. On the other hand, if the hydrogen pressure is higher than 20 atm, a high pressure-resistant equipment, which is usually very expensive, will be required and it is also disadvantageous from the standpoint of safety.

According to a preferred embodiment of the present invention, the hydrogenation reaction is carried out at a temperature of 150° to 230° C. under a pressure of 3 to 20 atm and in the presence of a catalyst selected from a chromium- or thorium-modified cobalt boride, wherein the modified cobalt boride is used in an amount of 2–15 wt % based on the weight of aniline. After completion of reaction, the reaction mixture is distilled to obtain pure, cyclohexylamine.

The present invention is now further illustrated with reference to the following Reference Examples and Examples.

REFERENCE EXAMPLE 1

Preparation of Cobalt Boride Catalyst and Nickel Boride Catalyst 20 mmol of cobalt acetate or nickel acetate was dissolved in 200 ml of deionized water and 60 mmol of sodium hydroboride ($NaBH_4$) was dissolved in 60 ml of deionized water separately. After complete dissolution, the aqueous solution of $NaBH_4$ was added slowly to the solution of cobalt acetate or nickel acetate, with gas bubbles evolved and black precipitates formed. After the evolution of gas bubbles ceased, the precipitates was separated from the solution and washed sequentially with deionized water (3 times), 95% ethanol (twice) and 99.5% ethanol (once) to obtain cobalt boride or nickel boride catalyst. Prior to addition to the reaction system, the catalyst was washed with aniline, a starting material of the reaction.

REFERENCE EXAMPLE 2

Preparation of modified cobalt boride and nickel boride

The modified cobalt boride and nickel boride are produced in the same manner as in Reference Example 1 with exception that a modifying agent selected from a salt of transition metal, e.g. organic or inorganic salts of chromium, thorium, molybdenum or iron, was added to the aqueous solution of cobalt acetate or nickel acetate prior to addition of the solution of sodium hydroboride to the solution of cobalt acetate or nickel acetate.

EXAMPLE 1

In a 1 L high pressure-resistant reactor, equipped with a pressure gauge, a temperature controller and a gas conduit provided with a dispersing disk, 800 g of aniline and 1.2 g (corresponding to 0.15 wt %, based on the weight of aniline) of a cobalt boride catalysts which was modified by various amount of chromium or thorium as listed in Table 1, were added. Nitrogen gas was introduced into the system to get the air out of the reactor. After the temperature in the reactor was raised to 180° C., hydrogen gas was introduced to the reactor to get nitrogen gas away and then the reactor was pressurized to 5.5 atm. The reaction continued for 10 hours while stirring at a rate of 700 rpm and maintaining the hydrogen pressure constantly at 5.5 atm. The product was analyzed by gas chromatography and the conversion percentage of aniline and the selectivity to cyclohexylamine were reported in Table 1.

COMPARATIVE EXAMPLE 1

Repeat the procedures of Example 1 except that non-modified cobalt boride was used as the catalyst. The conversion percentage of aniline and the sensitivity to cyclohexylamine were reported in Table 1.

COMPARATIVE EXAMPLE 2

Repeat the procedures of Example 1 except that 5% ruthenium/active carbon was used as the catalyst. The conversion percentage of aniline and the sensitivity to cyclohexylamine were reported in Table 1.

COMPARATIVE EXAMPLE 3

Repeat the procedures of Example 1 except that Raney cobalt (Tradename "Raney Co Catalyst R-400", purchased from Nikko Rica Corporation) was used as the catalyst. The conversion percentage of aniline and the sensitivity to cyclohexylamine were reported in Table 1.

COMPARATIVE EXAMPLE 4

Repeat the procedures of Example 1 except that non-modified nickel boride was used as the catalyst. The conversion percentage of aniline and the sensitivity to cyclohexylamine were reported in Table 1.

COMPARATIVE EXAMPLE 5

Repeat the procedures of Example 1 except that a nickel boride which was modified by various amount of chromium, thorium, molybdenum or iron was used as the catalysts. The conversion percentage of aniline and the sensitivity to cyclohexylamine were reported in Table 1.

COMPARATIVE EXAMPLE 6

Repeat the procedures of Example 1 except that a molybdenum-modified cobalt boride was used as the catalyst. The conversion percentage of aniline and the sensitivity to cyclohexylamine were reported in Table 1.

reaction temperature was varied as shown in Table 2, thereby studying the influence of the reaction temperature on the conversion percentage of aniline and the selectivity to cyclohexylamine. The results were reported in Table 2.

TABLE 1

| | catalyst | aniline conversion rate (%) | selectivity (mol %) | | | | | |
|---|---|---|---|---|---|---|---|---|
| | | | cyclohexylamine | dicyclohexylamine | benzene | cyclohexane | cyclohexanone | cyclohexanol |
| Ex.1 | 2% Cr/CoB | 9.34 | 93.73 | 2.66 | 0.08 | 0.73 | 0.07 | 2.73 |
| | 3.5% Cr/CoB | 10.02 | 93.06 | 2.59 | 0.28 | 0.16 | 0.15 | 3.76 |
| | 5% Cr/CoB | 13.24 | 93.48 | 2.21 | 0.27 | 0.10 | 0.17 | 3.77 |
| | 8% Cr/CoB | 9.50 | 92.37 | 2.99 | 0.09 | 0.39 | 0.11 | 4.06 |
| | 10% Cr/CoB | 5.90 | 81.13 | 5.37 | 0.00 | 1.09 | 0.72 | 11.69 |
| | 2% Th/CoB | 10.60 | 95.55 | 0.62 | 0.00 | 0.78 | 0.00 | 3.05 |
| | 5% Th/CoB | 10.62 | 96.15 | 0.67 | 0.25 | 0.05 | 0.13 | 2.75 |
| | 10% Th/CoB | 11.31 | 95.80 | 1.14 | 0.14 | 0.10 | 0.10 | 2.71 |
| | 15% Th/CoB | 9.87 | 93.43 | 2.53 | 0.08 | 0.42 | 0.01 | 3.54 |
| CEx. 1 | cobalt boride | 1.98 | 91.36 | 4.17 | 0.04 | 0.00 | 0.80 | 3.62 |
| CEx. 2 | 5% Ru/C | 0.56 | 71.55 | 13.77 | 0.05 | 12.15 | 0.23 | 2.25 |
| CEx. 3 | Raney cobalt | 4.44 | 97.97 | 0.55 | 0.00 | 0.00 | 0.12 | 1.36 |
| CEx. 4 | nickel boride | 4.00 | 95.05 | 3.62 | 0.34 | 0.00 | 0.18 | 0.81 |
| CEx. 5 | 2% Cr/NiB | 3.59 | 91.83 | 3.30 | 0.27 | 0.00 | 0.64 | 3.96 |
| | 5% Cr/NiB | 3.12 | 83.28 | 1.76 | 0.45 | 1.28 | 3.99 | 9.25 |
| | 2% Mo/NiB | 4.36 | 92.91 | 5.65 | 0.38 | 0.00 | 0.13 | 0.93 |
| | 5% Mo/NiB | 4.56 | 93.50 | 4.83 | 0.44 | 0.03 | 0.17 | 1.03 |
| | 10% Mo/NiB | 4.48 | 87.60 | 7.30 | 0.79 | 0.05 | 0.87 | 3.39 |
| | 2% Fe/NiB | 3.48 | 90.97 | 5.58 | 0.28 | 0.11 | 0.48 | 2.58 |
| | 5% Fe/NiB | 2.68 | 91.71 | 6.98 | 0.31 | 0.00 | 0.16 | 0.84 |
| | 2% Th/NiB | 4.36 | 94.42 | 4.49 | 0.48 | 0.00 | 0.03 | 0.57 |
| | 5% Th/NiB | 5.83 | 88.16 | 10.23 | 0.37 | 0.00 | 0.35 | 0.89 |
| | 8% Th/NiB | 4.70 | 86.67 | 10.87 | 0.19 | 0.03 | 0.56 | 1.70 |
| | 10% Th/NiB | 3.13 | 85.14 | 8.15 | 0.57 | 0.00 | 1.55 | 4.59 |
| CEx. 6 | 2% Mo/CoB | 2.98 | 89.99 | 3.52 | 0.00 | 1.73 | 0.00 | 4.76 |
| | 5% Mo/CoB | 1.49 | 88.72 | 2.08 | 0.19 | 0.24 | 1.22 | 7.54 |

Ex.: Example
CEx.: Comparative Example

EXAMPLE 2

Repeat the procedures of Example 1 except that 5% chromium/cobalt boride was used as the catalyst and the

TABLE 2

| reaction temperature (°C.) | aniline conversion rate (%) | selectivity (mol %) | | | | | |
|---|---|---|---|---|---|---|---|
| | | cyclohexylamine | dicyclohexylamine | benzene | cyclohexane | cyclohexanone | cyclohexanol |
| 130 | 1.87 | 95.34 | 2.21 | 0.00 | 0.00 | 0.01 | 2.44 |
| 150 | 6.12 | 94.97 | 2.36 | 0.00 | 0.41 | 0.11 | 2.15 |
| 180 | 13.24 | 93.48 | 2.21 | 0.27 | 0.10 | 0.17 | 3.77 |
| 185 | 13.46 | 94.00 | 2.92 | 0.40 | 0.16 | 0.11 | 2.40 |
| 190 | 14.47 | 93.38 | 2.99 | 0.45 | 0.03 | 0.18 | 3.40 |
| 200 | 15.13 | 93.03 | 2.22 | 1.21 | 0.06 | 0.22 | 3.26 |
| 230 | 19.71 | 91.43 | 5.34 | 0.47 | 0.75 | 0.00 | 2.01 |
| 250 | 21.22 | 81.52 | 15.08 | 0.51 | 1.42 | 0.00 | 1.47 |

From Table 2, it can be seen that the conversion percentage of aniline increased with elevation of the temperature. When the temperature was up to 250° C., however, the selectivity to cyclohexylamine significantly decreased and dicyclohexylamine, a by-product, greatly increased. Thus, the reaction temperature should not exceed 250° C.

EXAMPLE 3

Repeat the procedures of Example 1 except that 5% chromium/cobalt boride was used as the catalyst and the reaction pressure was varied as shown in Table 3, thereby studying the influence of the reaction pressure on the conversion percentage of aniline and the selectivity to cyclohexylamine. The results were reported in Table 3.

TABLE 3

| reaction pressure (atm.) | aniline conversion rate (%) | selectivity (mol %) | | | | | |
|---|---|---|---|---|---|---|---|
| | | cyclohexylamine | dicyclohexylamine | benzene | cyclohexane | cyclohexanone | cyclohexanol |
| 1 | 3.05 | 92.81 | 2.76 | 0.63 | 0.53 | 0.19 | 3.08 |
| 3 | 8.91 | 92.45 | 3.03 | 0.05 | 0.41 | 0.07 | 2.69 |
| 4.8 | 8.74 | 92.21 | 2.85 | 0.50 | 0.90 | 0.00 | 3.59 |
| 5.5 | 13.24 | 93.48 | 2.21 | 0.27 | 0.10 | 0.17 | 3.77 |
| 6 | 14.89 | 92.86 | 3.52 | 0.19 | 1.06 | 0.03 | 2.35 |
| 7.5 | 15.62 | 90.86 | 2.70 | 0.15 | 3.66 | 0.01 | 2.62 |
| 11 | 18.99 | 92.56 | 4.14 | 0.11 | 0.98 | 0.01 | 2.20 |
| 15 | 23.11 | 92.30 | 4.90 | 0.16 | 0.00 | 0.01 | 1.53 |
| 20 | 25.77 | 91.74 | 5.91 | 0.21 | 0.08 | 0.00 | 2.06 |

From Table 3, it can be seen that when the pressure was in the range of 1 to 20 atm, the conversion percentage of aniline increased with the elevation of the pressure, and the selectivity to cyclohexylamine was maintained over 90 mol %.

EXAMPLE 4

Repeat the procedures of Example 1 except that 5% thorium/cobalt boride was used as the catalyst and the amount of the catalyst was varied as shown in Table 4, thereby studying the influence of the amount of the catalyst on the conversion percentage of aniline and the selectivity to cyclohexylamine. The results were reported in Table 4 and the amount of the catalyst indicated therein was expressed in a weight percentage relative to aniline.

TABLE 4

| the amount of catalyst | aniline conversion rate (%) | selectivity (mol %) | | | | | |
|---|---|---|---|---|---|---|---|
| | | cyclohexylamine | dicyclohexylamine | benzene | cyclohexane | cyclohexanone | cyclohexanol |
| 0.15% | 10.62 | 96.15 | 0.67 | 0.25 | 0.05 | 0.13 | 2.75 |
| 0.60% | 69.92 | 97.82 | 0.23 | 0.05 | 0.21 | 0.32 | 1.37 |
| 2.0% | 86.01 | 97.00 | 1.90 | 0.11 | 0.09 | 0.05 | 0.85 |
| 5.0% | 91.30 | 97.46 | 1.05 | 0.10 | 0.11 | 0.09 | 1.18 |
| 15.0% | 95.84 | 98.03 | 0.38 | 0.14 | 0.00 | 0.09 | 1.35 |
| 20.0% | 95.38 | 94.90 | 3.72 | 0.02 | 0.00 | 0.07 | 1.29 |

EXAMPLE 5

Repeat the procedures of Example 1 except that 5% thorium/cobalt boride was used as the catalyst and the catalyst was repeatedly used, thereby studying if the activity of the catalyst will be reduced after repetitive use. The results were reported in Table 5.

TABLE 5

| the frequency of repetitive use of the catalyst | aniline conversion rate (%) | selectivity (mol %) | | | | | |
|---|---|---|---|---|---|---|---|
| | | cyclohexylamine | dicyclohexylamine | benzene | cyclohexane | cyclohexanone | cyclohexanol |
| 1 | 10.62 | 96.15 | 0.67 | 0.25 | 0.05 | 0.13 | 2.75 |
| 2 | 11.70 | 97.67 | 0.42 | 0.04 | 0.18 | 0.32 | 1.38 |
| 3 | 11.18 | 95.52 | 3.42 | 0.09 | 0.08 | 0.05 | 0.85 |
| 4 | 12.39 | 96.66 | 1.90 | 0.08 | 0.09 | 0.09 | 1.18 |

It can be seen from Table 5 that the activity of the catalyst was not significantly deteriorated after repetitive use of the catalyst.

It should be noted that the above examples are given only for illustration rather than establishing limitation to the present invention. The persons skilled in the art can make any change and modification within the spirit and scope of the present invention and these change and modification are also intended to be included in the present invention.

What is claimed is:

1. A method for preparing cyclohexylamine, comprising hydrogenating aniline at a temperature of 150° to 250° C. under a hydrogen pressure of 1 to 20 atm in the presence of a catalyst selected from a chromium- or thorium- modified cobalt boride, to obtain cyclohexylamine, wherein the amount of said modified cobalt boride is at least 0.6 wt % based on the weight of aniline.

2. The method according to claim 1 wherein the amount of chromium in said chromium-modified cobalt boride is 2–10 wt % based on the weight of cobalt boride; and the amount of thorium in said thorium-modified cobalt boride is 2–15 wt % based on the weight of cobalt boride.

3. The method according to claim 1 wherein said modified cobalt boride is used in an amount of 0.6–20 wt % based on the weight of aniline.

4. The method according to claim 3 wherein said modified cobalt boride is used in an amount of 2–15 wt % based on the weight of aniline.

5. The method according to claim 1 wherein said hydrogenation reaction is carried out under a hydrogen pressure of 3 to 20 atm.

6. The method according to claim 1 wherein said hydrogenation reaction is carried out at a temperature of 150° to 230° C.

7. The method according to claim 1 wherein said hydrogenation reaction is carried out at a temperature of 150° to 230° C. and a hydrogen pressure of 3 to 20 atm in the presence of a chromium- or thorium-modified cobalt boride, wherein said modified cobalt boride is used in an amount of 2–15 wt % based on the weight of aniline.

* * * * *